United States Patent [19]
Jian et al.

[11] Patent Number: 5,911,993
[45] Date of Patent: Jun. 15, 1999

[54] HOMEOPATHIC ANTIDIABETIC TREATMENT

[76] Inventors: Ding Jian; Ding Qing, both of Room 404, Building 108, Chengzeyuan, Beijing University, Beijing, China

[21] Appl. No.: 08/966,650

[22] Filed: Nov. 10, 1997

[30] Foreign Application Priority Data

Jan. 23, 1997 [CN] China .................. 97 1 00285

[51] Int. Cl.⁶ .......................... A61K 35/00; A61K 35/78
[52] U.S. Cl. ....................................... 424/195.1; 514/866
[58] Field of Search ................... 424/195.1; 514/866

[56] References Cited

FOREIGN PATENT DOCUMENTS

| 3-106819 | 5/1991 | Japan . |
| 5-178749 | 7/1993 | Japan . |
| 5-178749 A2 | 7/1993 | Japan . |

OTHER PUBLICATIONS

Men, "Studies on the Constituents of Sedum Alfredi", J. Taiwan Pharm Ass. 38 (1) pp. 52–66, 1986.

Boissya et al, "Some Folklore Claims from the Brahmaputra Valley", Ethnomedicine 6 pp. 139–145, 1980.

Chou, "Chrysoeriol 7-0-Rhamnoside from Sedum Formosanum", Phytochemistry 15 p. 1420, 1976.

*Primary Examiner*—Carlos A. Azpuru
*Assistant Examiner*—Brian K. Seidleck
*Attorney, Agent, or Firm*—Nixon & Vanderhye P.C.

[57] ABSTRACT

A highly effective pure, natural, ingestible antidiabetic may be made from Shilianhua (*Echevaria glauca, Sinocrassula berger,* Crassulaceae) by washing leaves and/or stems of the Shilianhua plant, crushing them in a grinder, breaking the cell walls to form a filterable material, filtering the material to produce a filtrate, and decompressing and concentrating the filtrate to produce a concentrated solution. The cell walls may be broken using medical alcohol, quick freezing and thawing, or ultrasonic mixing. The concentrated solution is then made into a powder, or concentrated powder, by baking, crushing, and passage through a 60 mesh screen; using a silica gel column; using a Saphadex column; or by treatment with a $CH_3COOC_2H_5$ solution. Treatment of, or to prevent, diabetes by lowering blood sugar at least 10% (e. g. about 50%) is practiced by daily administration of about 50–100 mg of powdered extract of *Echevaria glauca, Sinocrassula berger,* Crassulaceae, or about 20–40 mg of concentrated powdered extract of *Echevaria glauca, Sinocrassula berger,* Crassulaceae.

11 Claims, 2 Drawing Sheets

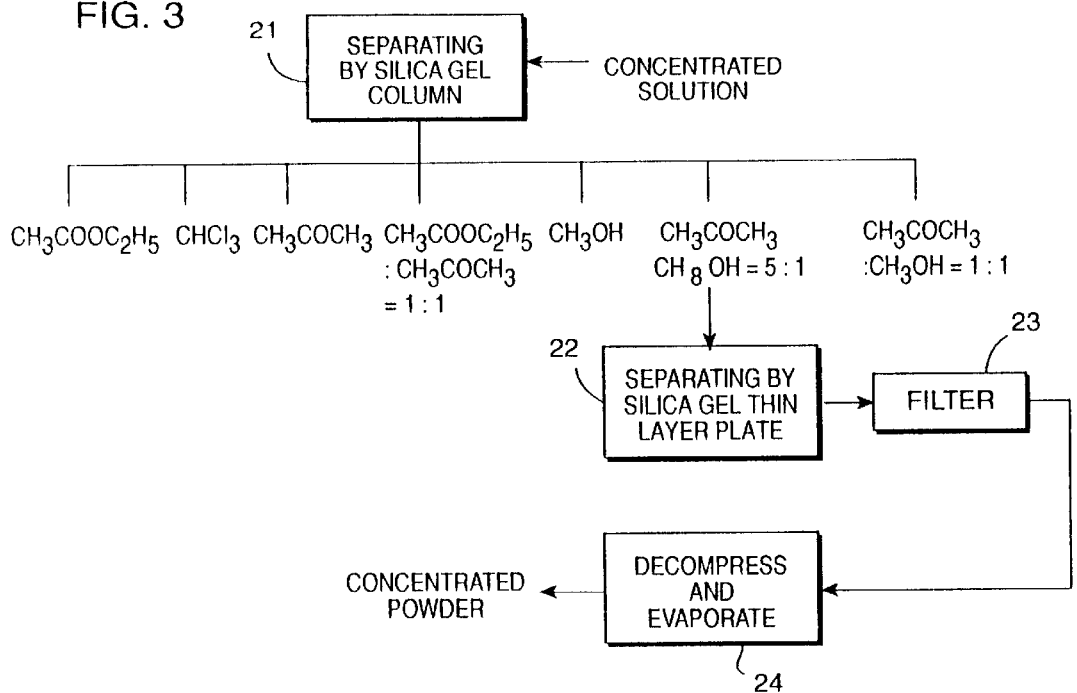
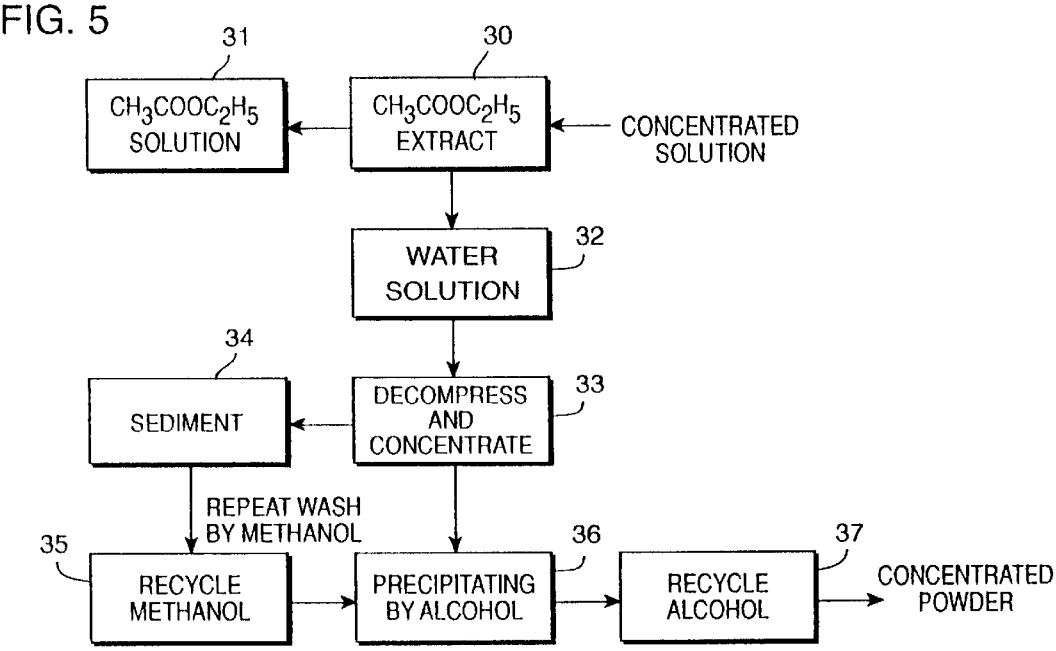

HOMEOPATHIC ANTIDIABETIC TREATMENT

BACKGROUND AND SUMMARY OF THE INVENTION

Diabetes, and particularly non-insulin dependent type diabetes, is the subject of a significant amount of research. A number of medicines have been produced and tested which act to lower blood sugar of a non-insulin dependent diabetic. However, the majority of these medicines have one or more undesirable features. Some of them have significant side effects for a large portion of the population, or a large dosage is necessary. Also, some of them reduce the blood sugar level too much so that they can only be used sporadically or they can be a threat to health, and others have possible toxicity. At present there is no natural antidiabetic drug which is highly effective at lowering blood sugar, yet does not lower it to an unsafe level, and has no significant side effects.

According to the present invention a pharmacologically active agent is produced in a simple and straightforward way using only a single natural source. The pharmacologically active agent according to the present invention is a homeopathic medicine that has no toxicity, is highly effective in reducing blood sugar for diabetics, and particularly non-insulin dependent diabetics, yet will not reduce toxicity too much. Relatively small amounts of the homeopathic medicine need be ingested in order to perform the desired function.

The raw material for making the homeopathic medicine according to the present invention—and for practicing methods of treating humans according to the present invention—is the wild plant typically known as "Shilianhua"(*Echevaria glauca*) or "Hehuazhang". This plant is in the family Crassulaceae, genus *Sinocrassula berger*, species *Echevaria glauca*. *Echevaria glauca, Sinocrassula berger*, Crassulaceae (which can be found in the China Annals of Plants, Volume 34, page 63, or Hebei Annals of Plants, Volume 1, pages 575, 576 Hort.ex Baker.in Saund. Refug.Bot. 1:sub T.61.1863-(Cotyledon glauca Baker)) can be found in some abundance in Mexico, and also in Bama county of Guangxi province in China. *Echevaria glauca, Sinocrassula berger,* Crassulaceae is a shrub that grows to a height of about 60 centimeters, with oppositely regularly branching leaves from the stem, providing a symmetrical, erect, very thick appearance. The leaves are shiny, blue-gray in color, obovoid or oblong-spatulated, with a length of between 5–8 centimeters, and a width of about 2.5–4 centimeters. The leaves are narrow at the base but not petioled. The plant typically blooms in June through August in the northern hemisphere.

The homeopathic medicine is made from *Echevaria glauca, Sinocrassula berger,* Crassulaceae alone using a wide variety of techniques. When the cell walls of the plant are broken, processing should be done at less than 60° C. so that the highly effective biological activity of the plant components is not adversely affected. Typically, the active ingredient from the *Echevaria glauca, Sinocrassula berger,* Crassulaceae plant is produced in the form of a powder, or concentrated powder. Non-insulin dependent patients typically would take 60–100 mg of the powder, or 20–40 mg of the concentrated powder, every day, and it is expected that when administered effectively the *Echevaria glauca, Sinocrassula berger,* Crassulaceae should be effective in more than 85% of the population. The powder can be produced using the cell wall breaking procedures such as shown in Chinese Patent No. 95117499.1.

According to one aspect of the present invention a method of treating a human patient having non-insulin dependent diabetes, to safely reduce the blood sugar concentration of the patient, is provided. The method comprises the step of (a) administering a pharmacologically effective amount of extract from plants of the family Crassulaceae, genus *Sinocrassula berger*, to a diabetic patient so as to reduce the blood sugar concentration of the patient. Typically, step (a) is practiced by administering *Echevaria glauca, Sinocrassula berger,* Crassulaceae. For example, step (a) is practiced by daily administering about 50–100 mg of powdered extract of *Echevaria glauca, Sinocrassula berger,* Crassulaceae, or about 20–40 mg of concentrated powdered extract of *Echevaria glauca, Sinocrassula berger,* Crassulaceae.

Step (a) is typically further practiced by administering the extract in substantially pure form, although it can be taken with foods, made into a tea, or mixed with inert materials or other pharmacologically active materials for other purposes. Step (a) is typically practiced by administering the extract in tablet or capsule form, although it may be taken intravenously as well as orally, in liquid form, as a gel, or in a wide variety of other manners.

Step (a) is typically practiced by administering a powder or concentrated powdered obtained by the steps of (a1) cleaning leaves and/or stems of Shilianhua; (a2) crushing the cleaned leaves and/or stems from step (a1); (a3) breaking the cell walls of the crushed leaves and/or stems from step (a2) to form a filterable composition; (a4) filtering the composition from step (a3) to form a filtrate comprising a concentrated solution of Shilianhua; and (a5) forming the concentrated solution from step (a4) into a powder or a concentrated powder.

The method according to the present invention is effective to reduce the blood sugar level of a typical patient by at least 10%, and typically at least about 30%, and in most cases in the order of around 50%. However, the blood sugar level will not be reduced far enough so as to cause adverse health consequences.

According to another aspect of the present invention a method of making an extract of "Shilianhua" (*Echevaria glauca*) is provided comprising the steps of: (a) Cleaning leaves and/or stems of Shilianhua. (b) Crushing the cleaned leaves and/or stems from step (a). (c) Breaking the cell walls of the crushed leaves and/or stems from step (b) to form a filterable composition. (d) Filtering the composition from step (c) to form a filtrate and then decompressing and concentrating the filtrate to produce a concentrated solution of Shilianhua. And (e) forming the concentrated solution from step (d) into a powder or a concentrated powder.

Step (c) may be practiced by soaking in medical alcohol, quick freeing and thawing, or ultrasonic mixing. Step (b) may be practiced by putting leaves and/or stems with water in an electric motor powered blender.

Step (e) may be practiced by baking the concentrated solution to produce a solid, then crushing the solid, and then passing the crushed solid through a screen, to form a powder. Alternatively, step (e) may be practiced by separating concentrated powder from the concentrated solution by separation using a silica gel column, and silica gel thin layer plates; or by passing the concentrated liquid into a Saphadex column, collecting eluted components, and decompressing and concentrating the eluted components, to produce a concentrated powder; or by extracting the concentrated solution using $CH_3CHOOC_2H_5$ solution, to produce a water solution, decompressing and concentrating the water solution, precipitating powder using substantially pure alcohol, and recycling the alcohol.

Steps (a) through (e) are typically practiced to produce about 225–250 g of powder, or about 9–95 g of concentrated powdered, from about 10 kilograms of *Echevaria glauca, Sinocrassula berger,* Crassulaceae.

According to another aspect of the present invention a method of producing and utilizing a pharmacologically effective agent of the family of plants Crassulaceae, genus *Sinocrassula berger,* is provided by practicing the steps of: (a) Cleaning leaves and/or stems of *Sinocrassula berger,* Crassulaceae plants. (b) Crushing the cleaned leaves and/or stems from step (a). (c) Breaking the cell walls of the crushed leaves and/or stems from step (b) to form a filterable composition. (d) Filtering the composition from step (c) to form a filtrate and decompressing and concentrating the filtrate to produce a pharmacologically active concentrated solution of *Sinocrassula berger,* Crassulaceae plants. (e) Making the pharmacologically active concentrated solution of *Sinocrassula berger,* Crassulaceae plants into human administrable form. And (f) administering the pharmacologically active Sinocrassula Crassulaceae in administrable form from step (e) to a human patient.

Step (f) is typically practiced to treat or prevent diabetes by reducing the blood sugar level of a patient by at least 10%. Step (a) is typically practiced by using *Echevaria glauca, Sinocrassula berger,* Crassulaceae. Step (e) may be practiced by using any one of the techniques as set forth above.

The invention also relates to a homeopathic medicine—a pharmacologically active substance—comprising a powdered extract of *Echevaria glauca, Sinocrassula berger,* Crassulaceae, produced by practicing the method as described above.

It is the primary object of the present invention to provide a safe, natural homeopathic medicine that is useful in effectively treating diabetes, and particularly non-insulin dependent diabetes. This and other objects of the invention will become clear from an inspection of the detailed description of the invention and from the appended claims.

BRIEF DESCRIPTION OF THE DRAWINGS

FIGS. 3 through 5 are schematic illustrations of methods for making concentrated powders of *Echevaria glauca, Sinocrassula berger,* Crassulaceae extract according to the present invention from the concentrated solution of the method of FIG. 1.

DETAILED DESCRIPTION OF THE DRAWINGS

Figure 1:
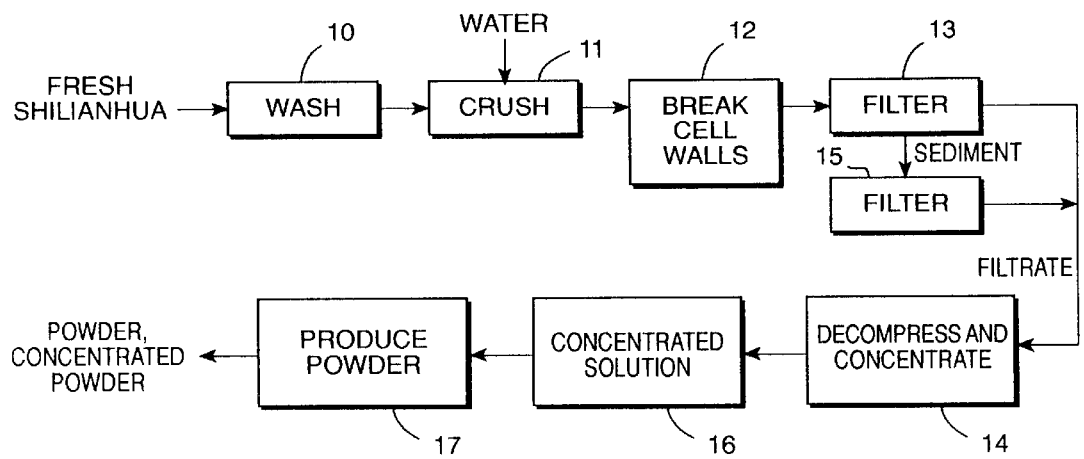
FIG. 1 is a schematic representation of various method steps that may be practiced to produce a suitable homeopathic medicine, in powder form, according to the present invention.

FIG. 1 schematically illustrates the basic steps in the manufacture of non-toxic homeopathic anti-diabetic medicine according to the present invention, which is an extract of Shilianhua. As illustrated in FIG. 1, fresh Shilianhua (typically leaves and stems, or only leaves, or only stems, may be used) is first washed as indicated in box 10 of FIG. 1 to clean it, and then it is crushed as illustrated in box 11 of FIG. 1. Crushing as illustrated in box 11 is typically accomplished by using a grinder or blender powered by an electric motor, and water may be added as indicated schematically in FIG. 1. Then the cell walls of the plants are broken, as indicated schematically by box 12 in FIG. 1.

A number of different techniques may be used for step 12 in FIG. 1. For example, one technique is to use medical alcohol. Using a mixture of about 50–70% ethyl alcohol. The alcohol itself may be added to the grinder. For example, if 10 kilograms of fresh Shilianhua is put into the grinder, four liters of 98% alcohol, adjusted so that the density of the liquid is about 70% by adding water or by providing moisture content from the plants, after the crushing step 11, is immersed overnight at ambient temperature (for example, at about 20–25° C.).

Another alternative is to practice step 12 by quick freezing and then thawing of the plant material. For example, after removal from the grinder the temperature of the material is quickly lowered to −20° C., and after freezing it is thawed quickly by heating until between about 40–50° C. Four hours after temperature equilibrium of the plant material has been reached four liters of distilled water is added (assuming 10 kilograms of fresh plant material in step 10) and the plant material is immersed overnight at ambient temperature in a water bath.

A third technique for practicing the step 12 of FIG. 1 is ultrasonic mixing. After grinding an ultrasonic cell crusher (such as a W220 type SONIGATOR) typically treats the plant material for five minutes at a frequency of about 800–900 Hz. Then four liters of distilled water are added (if 10 kilograms of fresh plant material in step 10) and the plant material is immersed in the distilled water at ambient temperature overnight.

Regardless of the technique used for breaking the cell walls in step 12, it is highly desirable to maintain the plant material at a temperature below 60° C. so as not to adversely affect the biological activity of the extract being produced.

After practicing step 12 a filterable composition is provided. The composition is filtered using a conventional filter as indicated schematically at 13 in FIG. 1. The filtrate from the filter in step 13 then passes to step 14, while the sediment is refiltered using the filter 15. The filtrate from the filter 15 is added to the filtrate from the filter 13. Typically the steps are repeated four times, and the filtrate from these five operations is passed to the decompression and concentration stage 14.

In the decompression and concentration stage 14, the filtrate is typically treated in a water bath at a temperature of about 60–70° C. to get 200 ml of concentrated liquid at a concentration of about 50 g/ml. The concentrated solution so produced, indicated schematically at 16 in FIG. 1, is then further treated as indicated by box 17 in FIG. 1 to produce a powder or concentrated powder.

Figure 2:
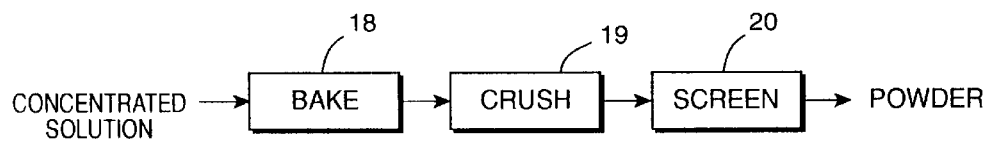
FIG. 2 schematically illustrates a method of producing a normal powder from the concentrated solution of the method of FIG. 1.

FIG. 2 shows one example of how the step 17 of FIG. 1 can be practiced. Taking the concentrated solution from stage 16 in FIG. 1, the solution is baked (dried at a temperature high enough to drive off the liquid, but not high enough to harm the material) as indicated at box 18 in FIG. 2, and then crushed (e.g. in a grinder) as indicated at box 19, and then screened as indicated in box 20. Screening may be accomplished utilizing a conventional 60 mesh screen through which the dried and crushed material is passed, producing a non-concentrated powder. For example, if 200 ml, with a concentration of 50 grams per milliliter, of solution is used in the method of FIG. 2 between about 225–250 grams of powder will be produced. The volume produced is dependent upon the particular step 12 utilized. Where medical alcohol techniques are used as step 12, one gets about 243 grams of powder, if a quick freeze-thaw technique is used for step 12, one gets about 239 grams of powder, and if the ultrasonic mixing technique is used for step 12, then one gets about 236 grams of powder.

FIG. 3 illustrates an alternative technique used as the step 17 in FIG. 1 for producing a concentrated powder. The concentrated solution from stage 16 in FIG. 1 is subjected to separation in a silica gel column as indicated schematically at 21 in FIG. 3. Column 21 is typically between about 100–150 mesh, 30×360. In order the solution is subjected to $CH_3COOC_2H_3$, $CHCl_3$, $CH_3COCH_3$, $CH_3COOC_2H_3:CH_3COCH_3=1:1$, $CH_3OH_2CH_3COCH_3:CH_3OH=5:1$, $CH_3COCH_3:CH_3OH=1:1$ to carry out non-linear elution. Then—as illustrated in FIG. 3—one collects $CH_3COCH_3:CH_3OH=5:1$ contents on the basis of the peak value of an ultraviolet monitor to make silica gel thin-layer plate 22 (GF254 10–40$\mu$) separation. Using $CH_3COOC_2H_5:CH_3OH:H_2O=4:0.6:03$ as developer, one collects Rf: 0.37–0.52 range contents on the thin-layer plate 22 and dissolves this content in the mixture $CH_3COCH_3:CH_3OH=5:1$. One then filters (23) and decompresses and evaporates Shilianhua (24) to dry it. One typically gets 17.01 g of concentrated powder, with gains ratio of 28%.

Figure 4:
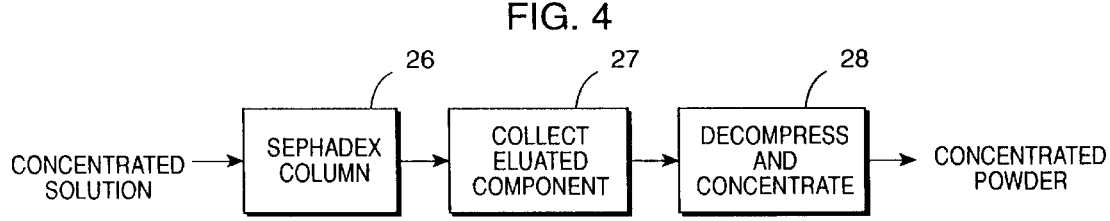

FIG. 4 shows yet another technique for producing concentrated powder as indicated schematically at 17 in FIG. 1. The concentrated solution from step 16 in FIG. 1 is fed to a SEPHADEX column 26 (e.g. a SEPHADEX LH-20 column, 50×1200) to carry a gradient elution using $CH_3OH$. Then the eluted component is collected as indicated at 27 in FIG. 4 on the basis of the peak value of an ultraviolet monitor, is decompressed and concentrated as indicated at 28 using the standard techniques, and a concentrated dry powder is produced.

FIG. 5 schematically illustrates yet another exemplary way that the step 17 in FIG. 1 can be practiced. Again, the concentrated solution from step 16 in FIG. 1 is utilized as the raw material and is subjected to $CH_3COOC_2H_5$ extraction as indicated schematically at 30 in FIG. 5, a $CH_3COOC_2H_5$ solution being produced as indicated at box 31 in FIG. 5, as well as a water solution as indicated at box 32. The water solution is decompressed and concentrated in box 33 in FIG. 5, using conventional techniques, and the sediment—box 34 in FIG. 5—is repeatedly washed with methanol. The methanol is recycled as indicated at 35. The washed sediment from 35 and the decompressed and concentrated water solution from 33 are precipitated using the substantially pure alcohol as indicated at 36 in FIG. 5, and the alcohol is recycled as indicated at 37. The concentrated powder of the extract is produced.

The powder or concentrated powder produced according to the procedures of FIGS. 2 through 5 typically has the following composition (in weight percent):

TABLE 1

| COMPOSITION | CONTENT (%) |
|---|---|
| protein | 30–52 |
| Total carbohydrate | 3.6–5.1 |
| polysaccharide | 3.5 |
| sapponin | 1.8 |
| water | 0.4–1.1 |
| fiber | 1.7 |
| trace elements | 3.0–7.3 |
| caffeine | <10 |
| (NaCl + KCl) | 0.58–1.25 |

Animal experimentations were done using the powder and concentrated power from the steps of FIGS. 2 through 5 in a maximum tolerated dose (MTD) experiment. The results of the experiment are as follows:

TABLE II

| Test Sample | Animal | The method of experiment |
|---|---|---|
| extract No.: 961688 Dried medicinal herbs: 3.6 g/ml | Mouse of Kumming species | 20 mice, weight 20 ± 2.5 g, half male and half female, fill empty gastric of mouse in the dose of 78 g/kg, fill all at one time, keep observing 7 days. All animals were quiet, with no abnormal conditions. Repeat once. This dose is 360 times the common dose for humans. |

Then, an animal experiment was conducted using a powder and concentrated powder from the methods of steps of FIGS. 2 through 5. The experimental method is as follows: Separate 88 Kumming species mice randomly to reference group, DSP group, DAS group, DAS 1, DAS 2, and DAS 3 groups, Damicron group, and Youjiangtang group, 11 female mice in each group. Use the mice to make diabetes models by injecting Tetraoxymidine, and compare experiment group with known DSP, Damicron, Youjiangtang (as the standard sample). The dose for every group: 0.5 mg/ml powder, every day 0.2 ml for every mouse, and every day 0.2 ml sodium chloride solution for the reference group only. Take blood to measure blood sugar value 6 days after filling the gastric. The results are:

TABLE III

| Group | Animal quantity | Sex | Blood sugar value (mg %) | | | Reducer rate | |
| | | | Before Use | After Use | $-X \pm SD$ | $(-\Delta X\%)$ | P value |
|---|---|---|---|---|---|---|---|
| DAS | 11 | F | 204.21 | 157.55 | 46.66 ± 36.85 | 46.66 | <0.01 |
| $DAS_1$ | 11 | F | 198.41 | 102.95 | 51.89 ± 40.99 | 51.89 | <0.01 |
| $DAS_2$ | 11 | F | 258.87 | 158.79 | 61.39 ± 36.82 | 61.39 | <0.001 |
| $DAS_3$ | 11 | F | 238.82 | 100.41 | 57.96 ± 39.25 | 57.96 | <0.01 |
| DSP | 11 | F | 295.36 | 159.15 | 46.12 ± 34.18 | 46.12 | <0.01 |
| YJT | 11 | F | 296.38 | 162.28 | 45.28 ± 37.05 | 45.28 | <0.01 |

TABLE III-continued

| | Animal | | Blood sugar value (mg %) | | | Reducer rate | |
|---|---|---|---|---|---|---|---|
| Group | quantity | Sex | Before Use | After Use | −X ± SD | (−ΔX%) | P value |
| DMC | 11 | F | 292.35 | 110.50 | 42.55 ± 38.61 | 42.55 | <0.01 |
| Ref. G | 11 | F | 180.67 | 176.98 | 2.04 ± 5.94 | 2.04 | — |

The sequence of reducing blood sugar is $DAS_2 > DAS_3 > DAS_1 > DSP > YJT > DMC$. $DAS_2$ is the most effective antidiabetic agent in all samples and shows very remarkable differences. The other groups, except for the reference group, also show remarkable differences.

Then, a teratogenesis experiment was run as follows:

(1) Experimental animal: Adopting 3 months old Wister rate provided by the animal faculty of China medical academy, raise 4 days in animal house whose temperature kept at 25° C.±1° C., humidity at 60~80%.

(2) Separating dose group: Adopting 200 times the clinical dosage (every adult 1 mg DAS powder per kg weight each day) as highest dose group, e.g. 200 mg/kg; and adopt other 2 dose group by decreasing ¾ dose progressively, e.g. 50 mg/kg, 12.5 mg/kg. Making another 1 positive (Acetyl salicylic acid 200 mg/kg) and 1 negative reference group; the quantity of mating rate for each group is 14~15.

(3) Medication: Adopting DAS (from FIGS. 2–5 powder) solution and 8.3% Acetyl salicylic acid to fill the gastric of each rat, using DAS 9 days from $6^{th}$ to $14^{th}$ days after becoming pregnant and using Acetyl salicylic acid 7 days from $8^{th}$ to $14^{th}$ days after becoming pregnant.

(4) The method of the experiment: To let male and female rats live together in the proportion of 2:1. At 6:00 PM every day, at 8:30 the next morning, check the genitals and sperm, which sperm discovered are regarded as mating rats, and count this day as 0 day. Measuring weight at 0 day, separating to every experimental group randomly and measuring weight at $5^{th}$, $10^{th}$, $15^{th}$, $20^{th}$ days and execute by using cervical vertebra dislocation, take fetus rat out and make routine inspection of outward appearance. Using Alizarin crimson decoration method to inspect skeletal terata and make viscera terata inspection.

The results are as follows:

TABLE IV

| Group | Weight increase of mother rat (P) | Live fetus rate of pregnant rat (P) | Terata of fetus rat outward skeleton viscera appearance | | |
|---|---|---|---|---|---|
| Experimental group | >0.05 | >0.05 | >0.05 | >0.05 | >0.05 |
| Negative Reference | — | — | — | — | — |

(6) Conclusion: Above results indicate that DAS of the experimental groups do not show remarkable difference with negative reference group (P>0.05) even though DAS dosage reaches 12.5, 50, 200 times of clinical dosage. Therefore it is determined that the powder of the invention is not a teratogenesis to Wister rats.

A mutation experiment is also run.

(1) Experimental method:

① Ames experiment: Taking 4 salmonella nutrition defect type strains (TA97, TA98, TA100, TA102), adopting flat dish mixing method to carry out direct causing mutation experiment and indirect causing mutation experiment induced by microsomease of mouse liver. The strains presented by Ames laboratory of the University of California are determined to be appropriate. Adopting 4 dose groups as 5, 50, 500, 1000 mg/dish plus a positive and a negative (natural recovery) reference group. Using 3 parallel samples in every experiment to do 2 times experiment and showing the results in average value. The colony whose recovery number exceeds 2 times of natural recovery number is recognized to be positive to causing mutation.

② Mouse marrow micronucleus experiment:

Adopting first class qualified Kumming species mouse (provided by animal house of CMA) whose weight are 24~30 g. Making 3 DAS dose groups as 10, 600, 1200 mg/kg plus a positive (cyclophosphamide 30 mg/kg, inject to stomach 2 times) and a negative reference group, 10 mice for each group, half male and half female. Filling the gastric of each mouse two days continuously, and executing the mouse 6 hours after last filling, taking sternum marrow to make thin section as routine, coloring to red. Counting 1000 polychromatic erythrocytes for each mouse, observing polychromatic erythrocytes which contains micronucleus and calculating the rate of micronucleus cell.

③ Mouse sperm terata experiment:

Adopting first class qualified Kumming species mouse (provided by animal house of CMA) whose weight are 27~36 g. Making 3 DAS dose groups as 10, 600, 1200 mg/kg plus a positive (cyclophosphamide 30 mg/kg, inject to stomach 5 days) and a negative reference group. Filling the gastric of each mouse for each of 5 days continuously, and executing the mouse at $35^{th}$ day after first filling, taking epididymis of both sides, coloring, observing 1000 sperms for each mouse and calculating the ratio of sperm mutation.

(2) Results:

① Amex experiment: The results are shown in Table V. The natural recovery number of these 4 strains is in the required range. All recoverey colony numbers of positive reference group exceed by 3 times the natural recovery number. The recovery colony number of 4 dose groups does not exceed by 2 times the natural recovery number, indicating that DAS in the range of dosage does not cause direct or indirect mutation to the 4 strains of typhic salmonella nutrition defect type.

TABLE V

| Dosage | TA 97 | | TA 98 | | TA 100 | | TA 102 | |
| --- | --- | --- | --- | --- | --- | --- | --- | --- |
| μg/dish | S 9 − | + | − | + | − | + | − | + |
| 0 | 177 ± 63 | 190 ± 29 | 37 ± 12 | 43 ± 8 | 192 ± 29 | 213 ± 29 | 315 ± 80 | 330 ± 78 |
| 5 | 170 ± 72 | 173 ± 32 | 36 ± 5 | 46 ± 9 | 213 ± 11 | 200 ± 42 | 356 ± 33 | 302 ± 77 |
| 50 | 175 ± 27 | 197 ± 44 | 38 ± 7 | 45 ± 6 | 175 ± 20 | 293 ± 25 | 311 ± 45 | 315 ± 57 |
| 500 | 185 ± 43 | 177 ± 46 | 36 ± 4 | 36 ± 7 | 183 ± 26 | 175 ± 18 | 336 ± 26 | 325 ± 10 |
| 1000 | 168 ± 32 | 183 ± 33 | 34 ± 4 | 34 ± 6 | 198 ± 21 | 208 ± 15 | 339 ± 45 | 314 ± 42 |
| 4NQNO(0.5) | 691 ± 156 | | 214 ± 51 | | 1820 ± 199 | | 930 ± 156 | |
| 2AA(12) | | 738 ± 169 | | 1041 ± 150 | | 1206 ± 109 | | 715 ± 30 |

② Mouse marrow micronucleus experiment: The results are in Table VI.

TABLE VI

| Group | Animal quantity | Analysed cell number | Ratio of cell micronucleus (%) |
| --- | --- | --- | --- |
| Negative R.G. | 10 | 10000 | 2.1 |
| Positive R.G. | 9 | 9000 | 45.3 |
| DAS10 mg/Kg | 10 | 10000 | 3.0 |
| DAS600 mg/Kg | 9 | 9000 | 2.8 |
| DAS1200 mg/Kg | 10 | 10000 | 3.2 |

The positive reference group has very remarkable differences compared to the negative group through X statistics analyses ($P<0.01$). The 3 experiment groups do not have any remarkable differences compared to the negative reference group ($P>0.05$). This result indicates that DAS in the above dose range does not induce the increase of micronucleus ratio of mouse marrow polychromatic erythrocytes.

③ Mouse sperm terata experiment: The result are shown in Table VII.

TABLE VII

| Group | Animal quantity | sperm number observed | Variant sperm number | Variant rate (%) |
| --- | --- | --- | --- | --- |
| Negative R.G. | 10 | 10000 | 137 | 13.7 |
| Positive R.G. | 10 | 10000 | 619 | 61.9 |
| DAS10 mg/kg | 10 | 10000 | 133 | 13.3 |
| DAS600 mg/Kg | 10 | 10000 | 130 | 13.0 |
| DAS1200 mg/Kg | 10 | 10000 | 147 | 14.7 |

The positive reference group has very remarkable differences compared to the negative group through statistics treatment ($P<0.01$). The 3 experiment groups do not have any remarkable differences compared to the negative reference group ($P>0.05$). This result indicates that DAS in the above dose range does not induce the sperm terata of mice.

The effects of causing mutation are not recognized in the range of experimental dose by synthesizing the above 3 experiments. DAS (the powder according to the invention) can be regarded as not likely to cause the mutation of somatic cells and germ cells.

A subchromic toxicity experiment was also conducted as follows:

(1) Experimental animal: First class Wistar weaning rat in 60~70 g weight range, provided by CMA.

(2) Group division and dosage: Dividing into 4 groups randomly, 24 rats for each group, half male and half female, 6 experimental groups and 1 reference group. Dividing experimental groups as low, medium, and high dosage group. The low, medium, and high dosages are equivalent to 10, 50, 100 times the human dose (1 mg/kg for 1 day) respectively, that is, the low dose, medium dose, and high dose are 10 mg/kg, 50 mg/kg, and 100 mg/kg, respectively.

(3) Observing items: Shown as Table VIII.

Hb: serum protein;

(WBC+DC): Total number of white blood cell and classify:

S-GPT: transaminase;

TG: glycerite;

CHO: Total cholesterol;

BUN: urea nitrogen

GLU: blood sugar

TP: Total protein;

Alb: albumin

Glb: globulin;

TABLE VIII 46 days serum biochemistry index, P value of (X ± SD)

| SEX | GROUP | Animal number | S-GPT mg/ml | GLU | BUN | CHO | TG | A/G | GLB g/dl | ALB | TP | Mb | Tota WBC 10,000/ mm | Lymph | Cell % neu- tro- phil | ac- ido- phil | mon- o- cyte |
| --- | --- | --- | --- | --- | --- | --- | --- | --- | --- | --- | --- | --- | --- | --- | --- | --- | --- |
| MALE | Low dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |
| | Med. dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |
| | High dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |
| | Ref. Group | 5 | >0.05 | >0.05 | >0.05 | >0.05 | >0.05 | >0.05 | '0.05 | >0.05 | >0.05 | >0.05 | >0.05 | >0.05 | >0.05 | >0.05 | >0.05 |
| FE- | Low dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |

TABLE VIII-continued 46 days serum biochemistry index, P value of (X ± SD)

| SEX | GROUP | Animal number | S-GPT mg/ml | GLU | BUN | CHO | TG | A/G | GLB g/dl | ALB | TP | Mb | Tota WBC 10,000/ mm | Lymph | Cell % neu- tro- phil | ac- ido- phil | mon- o- cyte |
|---|---|---|---|---|---|---|---|---|---|---|---|---|---|---|---|---|---|
| MALE | Med. dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |
|  | High dose | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |
|  | Ref. Group | 5 | >0.05 | >0.05 | >0.05 | >0.05 | >0.05 | >0.05 | >0.05 | >0.05 | >0.05 | >0.05 | >0.05 | >0.05 | >0.05 | >0.05 | >0.05 |

NOTE:
1. P values are all >0.05, means that they don't have remarkable difference with reference group.
2. Reference group doesn't have statistical meaning.

① Taking half of the animals at 45$^{th}$ day, half male and half female, taking blood from the tail to measure for analysis.

② 90 days DAS dose to rat: rat weight, quantity of taking food, blood, biochemistry routine index, and internal organs content coefficient are shown in Table IX.

TABLE IX

| SEX | Group | Animal quantity | Weight (P) | Quantity of taking food (P) | Blood routine index (P) | Blood bio- chemistry index (P) | Weight | Main internal organs index (P) Naked eye observing | Pathology inspection |
|---|---|---|---|---|---|---|---|---|---|
| M | Low d. | 12 | >0.05 | >0.05 | >0.05 | >0.05 | >0.05 | >0.05 | >0.05 |
|  | Med. d. | 12 | >0.05 | >0.05 | >0.05 | >0.05 | >0.05 | >0.05 | >0.05 |
|  | High d. | 11 | >0.05 | >0.05 | >0.05 | >0.05 | >0.05 | >0.05 | >0.05 |
|  | Ref. G. | 11 | >0.05 | >0.05 | >0.05 | >0.05 | >0.05 | >0.05 | >0.05 |
| F | Low d. | 12 | >0.05 | >0.05 | >0.05 | >0.05 | >0.05 | >0.05 | >0.05 |
|  | Med. d. | 11 | >0.05 | >0.05 | >0.05 | >0.05 | >0.05 | >0.05 | >0.05 |
|  | High d. | 12 | >0.05 | >0.05 | >0.05 | >0.05 | >0.05 | >0.05 | >0.05 |
|  | Ref. G. | 12 | >0.05 | >0.05 | >0.05 | >0.05 | >0.05 | >0.05 | >0.05 |

(4) Discussion:
① 45 days blood routine and serum biochemistry examination, and 90 days blood routine, serum biochemistry, pathology examination show that DAS (powder produced according to FIGS. 2–5) in the range of experimental dosage has no unhealthy effect on Wistar rat.

② The measured blood sugar values in above two experiments show that long period and high dose DAS used by Wistar rats which do not suffer from diabetes had not caused even 1 example of low or high blood sugar, but high blood sugar was observed in reference group. This result indicates that the DAS powder according to the invention has an effective two-way control of blood sugar.

All of the animal testing shows the homeopathic medicine according to the invention to be safe.

Clinical experiments were also conducted on humans from various provinces of China. Five examples of these clinical experiments are as follows (in each experiment each tablet had 20 mg of non-concentrated powder of *Echevaria glauca, Sinocrassula berger,* Crassulaceae according to the invention):

EXAMPLE 1

Kong X X, female, 58 years old, diagnosed as non-insulin dependent type diabetes on Jun. 15, 1993, had taken Xiaokewan, Yuxiaosan, Youjiangtan, Damicron medicine and gone on dietotherapy. The blood sugar value of the empty stomach varied in the range of 138~260 mg/dl. Stopping all other medicine to use DAS tablet containing DAS powder, starting Oct. 1, 1995. Three tablets were taken every day, before meals. The blood sugar value of her empty stomach decreased to 180 mg/dl, and glucose in urine (±) after 1 week. After 4 weeks the blood sugar value was reduced to 121 mg/dl (a reduction of more than 50% of the highest original levels) and glucose in urine (−).

EXAMPLE 2

Zhang X X, male, 48 years old, diagnosed as insulin dependent type diabetes on May 9, 1994, the blood sugar value of the empty stomach was 310 mg/dl, glucose in urine (++). Injecting 20 units insulin to keep the blood sugar in the range of 110~150 mg/dl, became high or low blood sugar occasionally. Used DAS tablet starting Oct. 2, 1995, 3 tablets each day, and decreased 15 units insulin at the same time. The blood sugar value of his empty stomach decreased to 130 mg/dl, and glucose in urine (±) after 1 week. After 4 weeks the blood sugar value of his empty stomach became 115 mg/dl and glucose in urine (−). Fluctuation between high and low blood sugar never appeared after taking the DAS tablets.

EXAMPLE 3

Li X X, male, 76 years old, diagnosed as non-insulin dependent type diabetes on Apr. 5, 1987, the blood sugar value was 260~300 mg/dl, had taken Xiaokewan and gone on dietotherapy; the blood sugar value of his empty stomach was controlled in the range of 135~180 mg/dl. Stopping all other medicine to use DAS tablet started Oct. 3, 1995, 2 tablets each day. The blood sugar value of his empty stomach became 140 mg/dl, and glucose in urine (±) after 1 week. After 4 weeks the blood sugar value decreased to 120 mg/dl and glucose in urine (-).

EXAMPLE 4

Oyang X, female, 51 years old, diagnosed as non-insulin dependent type diabetes on Feb. 3, 1988, the blood sugar value of empty stomach was 280 mg/dl, glucose in urine (++), had taken Youjiangtan, Damicron to keep the blood sugar of empty stomach in the range of 150~190 mg/dl and glucose in urine (++), but became dizzy after taking Youjiangtang (a sign of low blood sugar). Stopping the other medicine to use DAS tablet started Oct. 2, 1995, 3 tablets each day. The blood sugar value of her empty stomach decreased to 145 mg/dl, and glucose in urine (±) after 1 week. After 4 weeks the blood sugar value of her empty stomach became 107 mg/dl and glucose in urine (-). Low blood sugar never appeared during the 1 month testing period in which she took DAS tablets.

EXAMPLE 5

Sima X X, female 47 years old, diagnosed as non-insulin dependent type diabetes on Aug. 21, 1991, the blood sugar value of her empty stomach was 265 mg/dl and glucose in urine (++), had taken Youjiangtang, Jiangtangshu, Damicron, etc. The blood sugar value of her empty stomach was controlled in the range of 120~160 mg/dl and glucose in urine (±). Stopping all other medicine to use DAS tablet started Oct. 2, 1995 taking 3 tablets per day. The blood sugar value of her empty stomach reduced to 135 mg/dl and glucose in urine (±) after 1 week. After 4 weeks the blood sugar value decreased to 105 mg/dl and glucose in urine (-).

It will thus be seen that according to the present invention a highly effective method of treating a diabetic is provided, to safely reduce the blood sugar concentration of the patient. The amount of homeopathic medicine produced from *Echevaria glauca, Sinocrassula berger,* Crassulaceae according to the present invention that is administered to each patient may vary widely depending upon sex, age, ethnic origin, diet, or other factors but typically is in the range of about 50–100 mg of normal powder and between about 20–40 mg of concentrated powder extract. The method according to the invention may be practiced to treat the diabetic, or even to prevent an onset of diabetes because the material according to the invention is nontoxic. The material may be taken in any form, mixed with food, and other ingredients, or other pharmacologically active substances, or injected into the blood stream, or taken according to any other conventional technique. The invention naturally, effectively, and without toxicity or side effects, readily controls blood sugar levels so that they are within a desirable range.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and products.

What is claimed is:

1. A method of treating a human patient having non-insulin dependent diabetes to safely reduce the blood sugar concentration of the patient, comprising the step of (a) administering a pharmacologically effective amount of extract from plants of the family Crassulaceae, genus *Sinocrassula berger,* to a diabetic patient so as to reduce the blood sugar concentration of the patient.

2. A method as recited in claim 1 wherein step (a) is practiced by administering *Echevaria glauca, Sinocrassula berger,* Crassulaceae.

3. A method as recited in claim 1 wherein step (a) is further practiced by daily administering about 50–100 mg of powdered extract of *Echevaria glauca, Sinocrassula berger,* Crassulaceae, or about 20–40 mg of concentrated powdered extract of *Echevaria glauca, Sinocrassula berger,* Crassulaceae.

4. A method as recited in claim 3 wherein step (a) is further practiced by administering the extract in substantially pure form.

5. A method as recited in claim 4 wherein step (a) is further practiced by administering the extract in tablets or capsules.

6. A method as recited in claim 1 wherein step (a) is practiced by administering a powder or concentrated powder obtained by the steps of:
(a1) cleaning leaves and/or stems of *Sinocrassula berger,* Crassulaceae; (a2) crushing the cleaned leaves and/or stems from step (a1); (a3) breaking the cell walls of the crushed leaves and/or stems from step (a2) to form a filterable composition; (a4) filtering the composition from step (a3) to form a filtrate comprising a concentrated solution of *Sinocrassula berger,* Crassulaceae; and (a5) forming the concentrated solution from step (a4) into a powder or a concentrated powder.

7. A method as recited in claim 2 wherein step (a) is practiced to reduce the blood sugar level of the patient by at least about 30%.

8. A method of administering a pharmacologically effective agent from plants of the family Crassulaceae, genus *Sinocrassula berger,* by the steps of:
(a) cleaning leaves and/or stems of *Sinocrassula berger,* Crassulaceae plants;
(b) crushing the cleaned leaves and/or stems from step (a);
(c) breaking the cell walls of the crushed leaves and/or stems from step (b) to form a filterable composition;
(d) filtering the composition from step (c) to form a filtrate and decompressing and concentrating the filtrate to produce a pharmacologically active concentrated solution of *Sinocrassula berger,* Crassulaceae plants;
(e) making the pharmacologically active concentrated solution of *Sinocrassula berger,* Crassulaceae plants into human administrable form; and
(f) administering the pharmacologically active *Sinocrassula berger* Crassulaceae in administrable form from step (e) to a human patient to treat diabetes by reducing the blood sugar level of the patient by at least 10%, but not to a dangerously low level.

9. A method as recited in claim 8 wherein step (a) is practiced by using *Echevaria glauca, Sinocrassula berger,* Crassulaceae.

10. A method as recited in claim 9 wherein step (e) is practiced by forming the concentrated solution from step (d) into a powder or a concentrated powder by at least one of: baking the concentrated solution to produce a solid, then crushing the solid, and then passing the crushed solid through a screen, to form a powder; or separating concentrated powder from the concentrated solution by separation using a silica gel column, and silica gel thin layer plates; or passing the concentrated liquid into a saphadex column, collected eluted components, and decompressing and concentrating the eluted components, to produce a concentrated powder; or extracting the concentrated solution using $CH_3CHOOC_2H_5$ solution, to produce a water solution, decompressing and concentrating the water solution, precipitating powder using substantially pure alcohol.

11. A pharmacologically active substance produced by practicing the method of claim 9.

* * * * *